US010463880B2

(12) United States Patent
Hautvast et al.

(10) Patent No.: US 10,463,880 B2
(45) Date of Patent: Nov. 5, 2019

(54) MEDICAL INSTRUMENT FOR HIGH DOSE RATE BRACHYTHERAPY

(71) Applicant: KONINKLIJKE PHILIPS N.V., Eindhoven (NL)

(72) Inventors: Guillaume Leopold Theodorus Frederik Hautvast, Veldhoven (NL); Dirk Binnekamp, Borne (NL)

(73) Assignee: Koninklijke Philips N.V., Eindhoven (NL)

( * ) Notice: Subject to any disclaimer, the term of this patent is extended or adjusted under 35 U.S.C. 154(b) by 218 days.

(21) Appl. No.: 15/120,641

(22) PCT Filed: Feb. 10, 2015

(86) PCT No.: PCT/EP2015/052680
§ 371 (c)(1),
(2) Date: Aug. 22, 2016

(87) PCT Pub. No.: WO2015/128179
PCT Pub. Date: Sep. 3, 2015

(65) Prior Publication Data
US 2017/0007849 A1 Jan. 12, 2017

(30) Foreign Application Priority Data

Feb. 27, 2014 (EP) .................................... 14156931
Oct. 24, 2014 (EP) .................................... 14190322

(51) Int. Cl.
*A61N 5/10* (2006.01)
*A61B 34/20* (2016.01)
(Continued)

(52) U.S. Cl.
CPC ............ *A61N 5/1007* (2013.01); *A61B 34/20* (2016.02); *A61N 5/1001* (2013.01);
(Continued)

(58) Field of Classification Search
CPC ................ A61N 5/1001; A61N 5/1049; A61N 2005/1051; A61N 2005/1059;
(Continued)

(56) References Cited

U.S. PATENT DOCUMENTS 6,248,968 B1 6/2001 Suzuki et al.
6,261,219 B1 7/2001 Meloul et al.
(Continued)

FOREIGN PATENT DOCUMENTS

JP H03218775 A 9/1991
JP H07185017 A 7/1995

OTHER PUBLICATIONS

Rickey, D.W. et al., "A quality assurance tool for high-dose-rate brachytherapy", Med. Phys. Jun. 2010, 37(6): 2525-32.
(Continued)

*Primary Examiner* — Navin Natnithithadha
*Assistant Examiner* — Sunita Reddy (57) ABSTRACT

An applicator device (100, 200, 300) for use in interventional brachytherapy, wherein the applicator device (100, 200, 300) is configured to be inserted in, or near a region of interest within a living body, and the applicator device is defining a lumen (101, 201, 301) for receiving a radiation source (103, 203, 303), characterized in that the applicator device (100, 200, 300) comprises one or more sensor elements (102, 202, 302) each configured to generate an output signal indicative of whether or not the radiation source (103, 203, 303) is at a predetermined position in the lumen (101, 201, 301).

12 Claims, 5 Drawing Sheets

(51) Int. Cl.
 *A61B 5/06* (2006.01)
 *A61B 8/12* (2006.01)
 *A61B 8/00* (2006.01)

(52) U.S. Cl.
 CPC .............. *A61N 5/1049* (2013.01); *A61B 5/06* (2013.01); *A61B 8/12* (2013.01); *A61B 8/445* (2013.01); *A61B 2034/2051* (2016.02); *A61B 2034/2055* (2016.02); *A61B 2034/2061* (2016.02); *A61B 2034/2063* (2016.02); *A61N 2005/1024* (2013.01); *A61N 2005/1051* (2013.01); *A61N 2005/1059* (2013.01)

(58) Field of Classification Search
 CPC .......... A61N 5/1007; A61N 2005/1024; A61B 2034/2055; A61B 2034/2063; A61B 2034/2051; A61B 2034/2061; A61B 5/06; A61B 8/12; A61B 8/445; A61B 34/20
 USPC .......................................................... 600/1–8
 See application file for complete search history.

(56) References Cited

U.S. PATENT DOCUMENTS

| | | | |
|---|---|---|---|
| 6,311,084 B1* | 10/2001 | Cormack | A61N 5/1007 600/411 |
| 6,471,710 B1* | 10/2002 | Bucholtz | G01B 11/005 600/229 |
| 7,354,391 B2 | 4/2008 | Stubbs | |
| 9,895,556 B2 | 2/2018 | Bharat | |
| 2005/0101824 A1 | 5/2005 | Stubbs | |
| 2005/0251235 A1* | 11/2005 | Schlorff | A61N 1/403 607/101 |
| 2007/0129593 A1 | 6/2007 | Gueye et al. | |
| 2007/0265503 A1 | 11/2007 | Schlesinger et al. | |
| 2007/0269008 A1* | 11/2007 | Pomper | A61G 3/001 378/65 |
| 2008/0154085 A1* | 6/2008 | Jervis | A61N 5/1015 600/3 |
| 2010/0120679 A1* | 5/2010 | Xu | C07K 14/47 514/6.9 |
| 2010/0152521 A1* | 6/2010 | Price | A61N 5/1027 600/7 |
| 2010/0312038 A1* | 12/2010 | Shechter | A61N 5/1015 600/3 |
| 2011/0166410 A1* | 7/2011 | Gutierrez | A61B 19/5244 600/8 |
| 2013/0204072 A1 | 8/2013 | Verard et al. | |
| 2014/0005465 A1 | 1/2014 | Ribbing | |
| 2015/0182144 A1 | 7/2015 | Bharat et al. | |

OTHER PUBLICATIONS

Su, H. et al., "Real-time MRI-Guided Needle Placement Robot with Integrated Fiber Optic Force Sensing", Proceedings—IEEE International Conference on Robotics and Automation, May 2011.

Park, Yong-Lae et al., "Real-Time Estimation of 3-D Needle Shape and Deflection for MRI-Guided Interventions", IEEE/ASME Transactions on Mechatronics, vol. 15, No. 6, Dec. 2010.

* cited by examiner

MEDICAL INSTRUMENT FOR HIGH DOSE RATE BRACHYTHERAPY

CROSS-REFERENCE TO PRIOR APPLICATIONS

This application is the U.S. National Phase application under 35 U.S.C. § 371 of International Application Serial No. PCT/EP2015/052680, filed on Feb. 10, 2015, which claims the benefit of European Patent Application No. 14190322.9, filed on Oct. 24, 2014 and European Patent Application No. 14156931.9, filed on Feb. 27, 2014. These applications are hereby incorporated by reference herein.

FIELD OF THE INVENTION

The present invention relates to the field of interventional brachytherapy. More specifically, the invention relates to an applicator device for use in interventional brachytherapy, wherein the applicator device is configured to be inserted in, or near a region of interest within a living body, and the applicator device is defining a lumen for receiving a radiation source.

The invention further relates to a system for interventional brachytherapy comprising an applicator device for use in interventional brachytherapy, wherein the applicator device is configured to be inserted in, or near a region of interest within a living body, and the applicator device is defining a lumen for receiving a radiation source.

The invention further relates to a method for using a system for interventional brachytherapy comprising an applicator device for use in interventional brachytherapy.

The invention further relates to a computer program code means for causing a system for interventional brachytherapy to perform a method for using a system for interventional brachytherapy comprising an applicator device for use in interventional brachytherapy.

BACKGROUND OF THE INVENTION

Radiation source placement technology in brachytherapy is usually based on a system using ultrasound imaging or on a system using X-ray or computed tomography. Integrated into an applicator or a catheter, such a system for correct placement or localization is aimed to provide a correct radiation dose to tumorous tissue and to prevent excessive radiation of healthy tissue.

In treatments of e.g. prostate cancer, cervix cancer, tumors of the mouth and pharynx, lung cancer or liver cancer, there are two radiation therapy concepts commonly applied: the isotopic brachytherapy and the electronic brachytherapy. The main differences consist in the radiation energy which is considerably lower in electronic brachytherapy, providing radiation energy of e.g. max. 50 keV, (the radiation source can be turned off also) as well as in the treatment possibilities: in electronic brachytherapy, x-ray facilities as well as standard operation rooms might be used (short range and low mean energy of the radiation), which is not possible in isotopic brachytherapy, especially in so called high dose rate (HDR) brachytherapy. Generally, in isotopic brachytherapy, the radiation sources usually are millimeter sized seeds of radioactive isotopes, like e.g. the iridium isotope Ir-192, providing radiation energy in the range of 350 kV.

It is of common practice to spread out over time (or fractionate) a radiation therapy treatment. Brachytherapy is usually administered in a multiple fraction to allow normal cells time to recover. Tumor cells are generally less efficient in repair between fractions. The number of fractions and the dose to be administered during each fraction will depend on the treatment plan as well as the individual patient condition.

Usually, a plurality of applicator devices (or catheters) can be placed under real-time image guidance based on e.g. ultrasound (US) or x-ray, or it can be imaged after placement (based on e.g. computer tomographic CT techniques) or placed based on previously registered images, wherein a seed (or any radiation source) is pulled (where applicable robotically) through the applicator or through interstitially implanted catheters. The plurality of applicator devices are placed such that their respective tips are in contact with the tumor. This arrangement enables better control of the region to irradiate. Problems appear when it is required to displace the applicator, not least because one or several additionally required CT scans of the treatment area, or when the applicator moves between fractions of treatments, so that radiation exposure of the patient healthy tissue might be disadvantageously high, or alternatively that the radiation exposure of the tumor cell might be disadvantageously low. For example, in isotopic brachytherapy, imaging is done before each radiation session, wherein during the course of therapy e.g. about ten CT scans can be required to check if the applicator did not move since the last fraction.

An applicator device is known from US 2014/0005465. This application discloses a brachytherapy guidance system comprising at least one tissue sensor and an environment sensor for determining local tissue characteristics can be provided, e.g. based on spectroscopy measurements. By integrating tissue sensing functions in a brachytherapy system, the problems regarding low soft tissue contrast or missing information on the character of the irradiated tissue can be reduced or even mitigated.

It is a drawback of known interventional brachytherapy devices and systems that the quantity of radiation received by the tissue to radiate (the tumor), when irradiated by a radiation source, is difficult to assess and to monitor. Thus, the efficacy of the interventional brachytherapy is prone to mistakes.

SUMMARY OF THE INVENTION

It is an object of the invention to provide an applicator device of the kind set forth in the opening paragraph which enables better monitoring of a brachytherapy treatment plan as well as a more accurate assessment of the radiation delivered to the tissue to be irradiated.

According to a first aspect of the invention, at least one of the aforementioned objects is realized by an applicator device defined in the opening paragraphs characterized by one or more sensor elements each configured to generate an output signal indicative of whether or not the radiation source is at a predetermined position in the lumen of an applicator device.

The invention enables determining the position of a radiation source, or a seed, or any other object, inside the lumen of an applicator device. At a predetermined position, for example at a tip of the applicator device (preferably the tip in the vicinity of the tissue to be irradiated), a sensor element is arranged to generate an output signal indicative of whether or not the radiation source is at such predetermined position. The radiation source at such predetermined position causes the sensor element to generate an output signal. It will be understood that the absence of a signal is also an output signal. In other words, any position in the lumen of the applicator device where the radiation source causes the sensor element(s) to generate an output signal is a predetermined position; hence an applicator device may comprise more than one predetermined position as it will be further explained below.

The invention is advantageous in that the positioning of the radiation source, or seed is of critical importance in interventional brachytherapy, as said positioning of the radiation source is directly related to the radioactive radiation that an irradiated tissue will receive (the therapeutic dose is highly dependent on accurate source positioning towards the treated volume/tissue). Between the insertion of the applicator device and the delivery of the radiation source for treatment, as well as between fractions of treatment, patient movement may cause the dose delivery catheters (or applicator device) to move and/or bend, causing uncertainty about the dose that is subsequently delivered to the irradiated tissue. The applicator device according to the present invention alleviates the above drawback in allowing in vivo positioning and/or checking of the position of a radiation source. In other words, the applicator device according to the present invention is arranged to indicate if the radiation source has reached a predetermined position, or alternatively, allows tracking of such a radiation source in the applicator device (in an embodiment where the applicator device comprises a plurality of sensor elements). In other words, the present invention provides an independent verification of the dwell (i.e.: for brachytherapy, the position where the source should pause to release its radiation) position by integrating a sensing system in the dose delivery catheters, such that the presence of the radiation source in a certain position can be confirmed.

The invention is further advantageous in that it allows the use of applicator devices without important modification to an afterloader. The invention therefore enables easy determination of the radiation source by the commonly used afterloader, with provide for an accurate, yet economically advantageous solution. As applicator device are required under good medical practice to be sterile, the present solution can provide for either a sterile single treatment applicator device, or for an applicator device capable of being sterilized via known commercial means.

According to a second aspect of the invention the object is achieved, a method for assessing if a radiation source is at a predetermined position in a lumen of an applicator device, said method comprising the steps of providing an applicator device; providing a radiation source into the lumen of the applicator device; generating an output signal indicative of whether or not the radiation source is at a predetermined position in the lumen; detecting said output signal, and assessing, from the output signal, if the radiation source is at the predetermined position.

In an embodiment of the present invention, the one or more sensor elements are one of—a) one or more optical sensors, or—b) one or more ultrasound sensors, or—c) one or more electromagnetic sensors. The skilled person will think of numerous types of sensor elements that would fall within those aforementioned categories as it will be further discussed hereunder. The type of sensor element(s) to be used according to different embodiment of the present invention will namely be limited by its (their) size, by the imaging modality under which the therapy is to be achieved. The sensor element(s) to be used will need to be compatible with an application device, such as catheter, suitable to be inserted in a human or an animal. In addition, the expected use of the applicator device may dictate to abstain using certain sensor element(s) under given conditions, where for example, an electromagnetic sensor may not be suitable for use under MRI guidance, but could provide for an alternative sensor element when the applicator device is used under ultrasound imaging.

In an embodiment, the proposed optical sensor element(s) may comprise for example, an IR sensor, or a LED sensor, or a photoelectric sensor, or an optical fiber. The skilled person will see in those optical sensor elements the common property of being arranged for emitting an optical signal (or light signal), and sensing the presence of an optical signal (or light signal) which could be the same as the original signal, or a reflected, or refracted optical signal. Moreover, such optical sensor could be configured to be able to generate an output signal in the absence of an optical signal. It will be clear for the skilled person that the output signal being the presence of an optical signal or the absence of an optical signal depends on the chosen configuration of the sensor element as well as the reflecting property of the radiation source.

Alternatively, the sensor element(s) may comprise an ultrasound sensor. Such sensor elements are arranged for emitting an ultrasound signal, and sensing the presence of an ultrasound signal, which could be the original transmitted ultrasound signal, or a reflected, or a refracted signal. Such ultrasound sensor could be configured to be able to generate an output signal in the absence of such ultrasound signal. It will be clear for the skilled person that the output signal being the presence of an ultrasound signal or the absence of an ultrasound signal depends on the chosen configuration of the sensor element.

Alternatively, the sensor element may comprise an electromagnetic sensor which could, for example, be either a capacitor, alternatively a resistor, alternatively a coil. In other words, in case of a magnetic sensor, a magnetic field could be generated by (the passage of) the radiation source, said magnetic field being detectable by the sensor element. For example, the electromagnetic sensor could be arranged such that, when at the predetermined position, the radiation source closes an electric circuit. This electric circuit closed by the radiation source generates an output signal. Such electromagnetic sensor could also be based on a change in capacitance when said the radiation source is present at the predetermined position.

In an embodiment, the one or more sensor elements comprise one or more optical sources for emitting an optical signal into the lumen and one or more optical receivers for receiving the optical signal from the lumen. An optical signal may be any electromagnetic signal in the wavelengths spectrum from extreme ultraviolet to far infrared. This embodiment has the advantage of providing a cost efficient, easy to manufacture applicator device arranged for adequately generating a sensor signal whether or not the radiation source is at the predetermined position. The skilled person will understand that a light signal is defined either by the presence of light, or the absence of light. To the extent the radiation source is, when at a predetermined position, blocking the light emitted by the optical source, the optical receiver will cease receiving the light signal from the lumen, blocked by the radiation source, which will indicate the presence of radiation source at a predetermined position. Alternatively, the radiation source may comprise reflecting element(s) which will, once said radiation source is positioned at a predetermined position, reflects the light emitted into the lumen by the light source to the optical receiver, which will then receive the optical signal from the lumen.

In yet another embodiment, the applicator device further comprises one or more optical fibers coupled to, at least one of the one or more optical sources, or at least one of the one or more optical receivers. This embodiment is advantageous in the sense that the applicator device is simple, robust and is easy to manufacture. Moreover, the presence of one or more optical fibers allow easy connectivity of the applicator device to be connected with a system for brachytherapy, as it will be further elucidated later on. Additionally, optical fibers are an easy mean for carrying an optical signal into and out of the lumen of an applicator device. It will be understood that in this embodiment, the optical source and the optical receiver could be the tip of an optical fiber; said optical fiber arranged to guide the optical signal in and out of the one or more optical fibers.

In another embodiment, at least one of the one or more optical fibers comprise fiber Bragg gratings. As fiber Bragg grating (FBG) can be defined as a type of distributed Bragg reflector constructed in a short segment of optical fiber arranged to reflect particular wavelengths of light and transmits all others. Such arrangement enables a more precise determination of the presence of the radiation source from a strain of the applicator, as to assess whether or not the radiation source is at the predetermined position. This construction has the further advantage of providing for a highly sensitive sensor element which is less prone to defect due to contamination, such as tissue or fluid.

In another embodiment, a plurality of Bragg reflectors are dispersed along the length of the optical fiber (at least partially the length of the applicator device), such that the optical signal is at least partially reflected by the fiber Bragg grating. This arrangement has the advantage of allowing a system to determine, from a detected optical signal, a change in shape and/or in temperature along the applicator device. This arrangement is made possible by the reflection of the one or more particular wavelengths, in addition by being arranged to determine whether or not the radiation source is at the predetermined position indicative of a temperature and/or strain of the applicator device. More particularly, this arrangement enables the determination of the radiation source at a predetermined position simultaneously than shape-sensing, and/or temperature sensing, which permits a better assessment of the influence of the radiation source with the applicator device. Once the radiation source is i) inserted in a applicator device, or ii) stable in the applicator device (the predetermined position), or iii) retrieved from the applicator device, a change of shape and/or temperature of said applicator device can be determined, enabling a better monitoring of the therapy.

In a yet other embodiment the one or more sensor elements comprise one or more ultrasound sources for emitting an ultrasound signal into the lumen and one or more ultrasound receivers for receiving an ultrasound signal from the lumen, wherein the one or more ultrasound sources and the one or more ultrasound receivers are positioned relative to each other such that the emitted ultrasound signal is either blocked from reaching the one or more ultrasound receivers or redirected to the one or more ultrasound receiver when such radiation source is at the predetermined position. This embodiment has the advantage of providing for alternative sensor elements which could adequately allow determination of a radiation source at a predetermined position in the lumen of an applicator device. In this embodiment ultrasound sensor(s) will have to be made in a way that they are small enough to generate an ultrasound wave into the lumen.

In another embodiment said one or more sensor elements are arranged, (i) to detect a change of electrical conductivity, or (ii) to detect a change of capacitance, or (iii) to generate an induction of electrical current, or (iv) to detect a change of resistance, indicative of whether or not the radiation source is at the predetermined position. This embodiment provides for alternative sensing elements to the one mentioned above which may be advantageous when the brachytherapy treatment is under guidance of certain imaging modalities.

In another embodiment the applicator device comprises at least two of the one or more sensor elements, wherein said at least two of the one or more sensor elements are arranged such that they generate an output signal allowing tracking of the radiation source into the lumen. This arrangement has the advantage that, to the extent those sensor elements are arranged in different longitudinal axis measured from the applicator device that the displacement of the radiation source may be monitor, enabling adequate monitoring of the therapy.

According to the invention, at least one of the foregoing objects is realized by a system for interventional brachytherapy comprising a detector unit configured to detect the output signal generated by each of the one or more sensor elements. This embodiment is advantageous as it enables detection of the radiation source into the lumen of an applicator device. The detector is configured to detect the output signal generated by the one or more sensor elements, such output signal indicative whether or not the radiation source inside the lumen of such applicator device is or reached a predetermined position. An example of the predetermined position could be the tip of the applicator device in the vicinity of the tissues to be irradiated.

In another embodiment, the system further comprises a tracking unit configured to track the movement of the radiation source in the lumen. Said tracking unit being arranged to received detected output signals enabling tracking of the radiation source in the lumen (when in use with an embodiment comprising at least two of the one or more sensor elements). Tracking (or tracing, or following) of the radiation source in the lumen is achieved by the detection of alternative output signals. Such alternative output signals are generated by alternative stimulation of sensors elements by the radiation source; such sensor elements being arranged to generate an output signal whether or not the radiation source is at a predetermined position in the lumen of the applicator device. Tracking the radiation source into the applicator device has the advantage of allowing locating a kink (a curve or a twist in the applicator device), if present. Additionally, this arrangement has the advantage of providing quality assurance on the time that the source spends in each dwell position (i.e.: for brachytherapy, the position where the source should pause to release its radiation).

In another embodiment, the system further comprises a signal generator arranged to generate a generation signal to be communicated the lumen. This arrangement has the advantage that the signal to be sent into the lumen originates from the system, rather than from the applicator device. This arrangement enables a better control over the signal, advantageously allowing a better precision of said signal (e.g.: in number of the wavelengths). This arrangement is further advantageous as it permits the use of smaller and more robust applicator devices for the brachytherapy treatment. The signal generator could be directly coupled to guiding means of the applicator device (i.e.: elements that will guide, lead a generated signal from the signal generator to the signal source), or may be indirectly coupled to such guiding means (e.g.: optically coupled).

In an embodiment, the signal generator is arranged to generate one or more optical generation signals of a predefined wavelength or of a predefined wavelength range. Alternatively, the signal generator is configured to generate said one or more optical generation signals simultaneously or successively. This arrangement has the advantage of improving the accuracy of the shape sensing and temperature sensing, while allowing the tracking of the radiation source.

In another embodiment the system further comprises a processing unit arranged to process the detected output signal(s). This processed detected output signal(s) to determine a) a temperature and/or shape of the applicator device, or b) a change in the temperature and/or the shape of the applicator device resulting from the radiation source being (i) deployed into the lumen, and/or (ii) at the predetermined position, and/or (iii) retrieved out of the lumen. In this embodiment, the processing unity is configured to process the one or more output signals generated by the fiber Bragg grating alternatively, the processing unit is configured to make use of Raleigh scattering to detect shape and/or temperature sensing. This arrangement is advantageous in that information as to the quantity of radiation emitted to the tissue may be inferred. Another advantage of this arrangement is that the processed detected signal may enable the system to stop as security measures if said signal is outside a certain predefined threshold.

In another embodiment the system further comprises a user interface unit configured to represent (or to depict or to show) the position (or the location) of the radiation source in the lumen. Additionally or alternatively, the user interface unity may be arranged for representing the movement of the radiation source in the lumen. This arrangement has the advantage of enabling quick and adequate process of information by a human brain, hence allowing quick reaction, response, or any other active or passive action(s) from the operator and/or the user. Such embodiment is further advantageous in allowing an operator to quickly see the movement of the radiation source into the lumen (when the system comprises a tracking unit) by visual representation.

In an embodiment, the system further comprises an alarm generator unit configured to generate an alarm when it is determined that the position and/or the movement of the radiation source in the lumen violates a predetermined limit based on the detected output signal. As a radiation source is radioactive and may potentially cause damages to healthy tissues are high, this arrangement is advantageous as the alarm may quickly trigger a user to act. Such alarm may be for example a visual signal, an audio signal, or any other means capable of catching the attention of the operator (or the user) such that a quick signal that may trigger the operator to take action(s) may is provided.

The method according to the invention is characterized in that within an applicator device as defined above a position and/or a movement of a radiation source into the lumen may be determined. The foregoing is achieved namely by the steps of providing an applicator device, providing a radiation source into the lumen of the applicator device, generating an output signal indicative of whether or not the radiation source is at a predetermined position in the lumen; detecting said output signal, assessing, from the output signal, if the radiation source is at the predetermined position.

The above described method provides the same benefits as the system for brachytherapy according to the first aspect of the invention. This method, when used in a system comprising the different embodiments described above, has similar advantages as the corresponding embodiments of the system. The proposed method is advantageous in that it enables a system for interventional brachytherapy to determine the position, or alternatively permits tracking of a radiation source in the lumen of an applicator device, such that the operator of the system may have easy access to the information on the radiation source in vivo.

According to the invention, at least one of the aforesaid objects is realized by a computer program comprising program code means for causing, when executed, a system for interventional brachytherapy, to carry out the steps of the method as defined above. This arrangement is advantageous as it enables fully automation of the method discussed above on a system for interventional brachytherapy, For example, the computer program permits that a robot, or any other machines to proceed with the steps of the method described above. Automation is advantageous in that it enables protection of an operator from any radiation emitted, or generated by the radiation source when used in a system for interventional brachytherapy.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

BRIEF DESCRIPTION OF THE DRAWINGS

These and other aspects of the applicator device, the system and the method according to the invention will be further elucidated and described with reference to the drawing, in which:

FIG. 1a-c schematically shows an embodiment of an applicator device according to the present invention.

FIG. 3a-b schematically shows a cross-section view of an embodiment of the applicator device according to the present invention.

DETAILED DESCRIPTION OF EMBODIMENTS

Certain embodiments will now be described in greater detail with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well known functions or constructions are not described in detail since they would obscure the embodiments with unnecessary detail. Moreover, expressions such as "at least one of", when preceding a list of elements, modify the entire list of elements and do not modify the individual elements of the list.

An applicator device 100 according to the present invention can be a catheter for brachytherapy, a needle or any hollow device in which a user, or an operator would be interested in adequately knowing if a radiation source 103 (or a seed) inserted therein is, or is not, at a predetermined position of interest, or alternatively if such user or such operator is interested in tracking the movement of such radiation source 103 in the applicator device 100. A radiation source 103 may be a solid, or alternatively a radioactive solid or even a liquid to the extent the liquid has a viscosity enabling detection. In further details, the radiation source 103 has a dimension in the order of the milliliters and comprises $^{195}$I, or alternatively $^{125}$I.

Figure 1A:
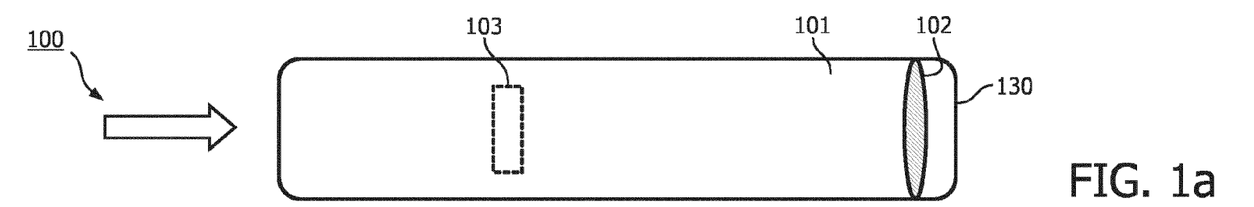

FIG. 1a comprises an applicator device 100, or a catheter according to the present invention. In this embodiment, the applicator device 100 forms of a circular hollow shape defining a lumen 101. Preferably said applicator device 100 is made of plastic, or alternatively silicones, alternatively polyvinyl chloride (PVC), or alternatively latex rubber, or alternatively metal. The skilled in the art will understand that any biocompatible flexible material could be used for the external envelop (outer wall 120) of the applicator device 100 according to the present invention. The applicator device 100 comprises an outer wall (in contact with the surrounding environment) 120 and an inner wall (defining the boundaries of the lumen) 121. An applicator device 100 for use in interventional brachytherapy will have at least one of, or both walls 120, 121 made of stainless steel or, alternatively polyoxymethylene in order to limit, or attenuate, or preferably block the radioactive radiations emitted by the radiation source 103 inserted in the applicator device 100 to reach the surrounding environment via the outer walls 120.

The radiations source 103 is arranged for being displaceable in the lumen 101 between two extremities of the applicator device. One of those extremities is arranged for receiving the radiation source 103 from an afterloader (not shown). A second extremity of the applicator device is arranged for being inserted in a human or animal body such that it is in the vicinity of the tissue to irradiate (hence where the interventional brachytherapy treatment needs to be carried). It will be understood that in use, one of those two extremities will be inserted into the body of the human or animal, while the other extremity will be outside the body such that a radiation source can be inserted therein by an afterloader (e.g.: the inserting end).

The applicator device according to FIG. 1a further comprises one sensor element 102 which is positioned near the tip, or at the tip 130 of the applicator device 100 arranged to be inserted in the human or animal living. Such position of the sensor element 102 corresponds to a preferred location relative to the applicator device 100. Alternatively, the number of sensor elements 102 could be more than one, for example 2, or 3, or 5, or 10 or even more. Having a plurality of sensor elements 102 may be advantageous as it will be further elucidated (e.g.: for tracking) The one or more sensor elements 102 can be positioned at any location relative to the applicator device 100 such that each of the one or more sensor elements 102 are arranged to generate an output signal indicative of whether or not the radiation source 103 is at a predetermined position.

The location of the one or more sensor elements 102 corresponds to a position of interest of the radiation source 103 into to the lumen of the applicator device 100. To the extent an applicator device 103 comprises more than one sensors, several positions of interest will be found in said applicator device 100. As mentioned above, a position of interest may be the tip of the applicator device, but could also be in the middle position of the applicator device 100, such that the output signal generated by the sensor element 102 at such position is indicative that the radiation source 103 has reached half of the distance between the inserting end of the applicator device 100 and the tip 130 of said applicator device (in close vicinity of the tissue to be irradiated). The predetermined position is usually defined by a point, or a distance range of several millimeters within the lumen 101, such that the output signal generated by the one or more sensor elements 102 is indicative of the radiation source 103 being within the boundaries of this range, hence being at the position of interest.

In an embodiment, the sensor element 102 is an optical sensor. Said sensor element 102 may be located between the inner wall 120 and outer wall 121 of the applicator device 100 alternatively, such sensor element may be coupled to the inner wall 102 located at least partially inside the lumen 101. Alternatively, said sensor element 102 may be located fully inside the lumen 101. Alternatively, said sensor element may be coupled to the applicator device 100 such that an output signal is capable of being generated by such sensor elements 102 when the radiation source is at the predetermined position. It is to be noted that the present invention also relates to one or more sensor elements 102 being ultrasound sensors, and alternatively an electromagnetic sensors.

Figure 1B:
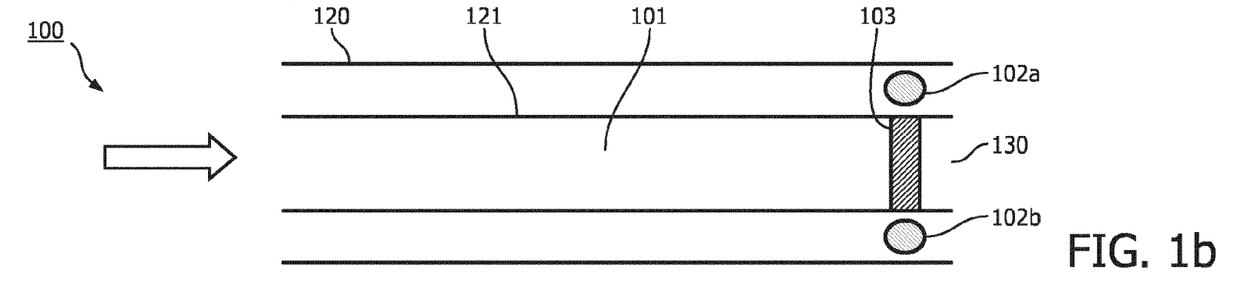

The one or more sensor elements 102 as optical sensors or ultrasound sensors will be further explained with the means of FIG. 1b. In an embodiment, the sensor elements 102 consist of an electromagnetic sensor arranged to either i) detect a change in the electrical conductivity; or ii) detect a change in the capacitance; or iii) generate an induction in the electrical current; or iv) detect a change in the electrical resistance. The skilled person will foresee several sensor elements means capable of forming those types of electromagnetic sensors when the radiation source 103 is made of conductive material. For example, when the sensor element 102 is a magnetic sensor, a magnetic field could be generated by (the passage of) the radiation source 103 at the location of the magnetic sensor. The magnetic field enabling said sensor element 102 to generate an output signal. In an alternative embodiment, the output signal may be consequential of the radiation source 103 closing an electric circuit when said radiation source is at the predefined position (which is the location, or within a range of few milliliters of the location of the sensor element 102). Alternatively, the electromagnetic sensor could also be characterized by a change of capacitance when the radiation source is at the predetermined position.

The output signal is generated when the radiation is indicative of the radiation source 103 being at a predetermined position. When an output signal is generated by, a sensor elements 102, the radiation source 103 is provoking a change of behavior in the sensor element 102 when at the position of interest, as it will be further elucidated by the means of FIG. 1b. For the sake of clarity, the inhibition of an initial signal when the radiation source 103 is at a predetermined position (in comparison to the generation of an initial signal when the radiation source is not at a predetermined position) is to be seen as an output signal. As it will be clear from the below, several means can be foreseen to enable the generation, or the inhibition of a signal when an object (i.e.: the radiation source) interacts with a sensor element 102. Interacting with the sensor element 102 must be interpreted broadly as being coupled to said sensor element 102, or alternatively in a close vicinity of said sensor element 102, or next to said sensor element 102, as to enable said sensor element 102 to generate an output signal indicative of the radiation source being at a predefined position.

FIG. 1b represents a cross-sectional view of an embodiment of the applicator device according to the present invention. Each of the one or more sensor elements 102 are further defined with a signal source 102a and a signal receiver 102b. The signal source 102a is arranged to emit an initial signal into the lumen 101, the signal receiver 102b is configured to receive an emitted signal from the lumen 101. In a preferred embodiment, the signal source 102a and the signal receiver 102b are positioned opposite to each other in an axis perpendicular to the applicator device 100. In this configuration the sensor element 102 is arranged such that the emitted signal received from the lumen by the signal receiver 102b is the original signal as emitted by the signal source 103a in the absence of the radiation source at the predetermined position.

Alternatively the position of the optical source 102a and the optical receiver 103b) relative to each other may differ than described above such that the expected objective is met. The light emitted in the lumen may therefore easily be received by the optical receiver, or alternatively be reflected until the source blocks (or further reflected with a different intensity) the optical signal. The signal source 102a and the signal receiver 102b may be positioned relative to each other such that an angle between 45 and 180 degrees is formed when measured on a plane perpendicular to the longitudinal axis of the applicator device 100. In this configuration, the initial signal may be reflected, or refracted, or absorbed by the radiation source 103 when said radiation source 103 is at the predetermined position such that an output signal is generated.

In an example embodiment of the present invention, the sensor element 102 is an optical sensor. In this embodiment, the sensor element is configured to i) emit light into the lumen 101, and ii) receive light from the lumen. The foregoing may be achieved by at least one optical source 102a for emitting an optical signal into the lumen 101 and one or more optical receivers 102b for receiving emitted optical signal from the lumen 101. Several means may be foreseen for the optical source(s) 102a, for example a light source (e.g.: a LED, an OLED, a laser), or alternatively, the tip of an optical fiber arranged such that a light signal guided by said optical fiber may go into the lumen 101. The present invention is not limited to a specific, or a range of optical wavelength; several optical wavelengths that could be optimal for the aforementioned construction (schematically shown in FIG. 1b), where the emitted optical signal by the optical source 102a does not need to be in the visible spectrum; hence the optical receiver 103b will be chosen accordingly.

The optical receiver 102b is arranged for receiving emitted optical signal from the lumen 101 in the presence of the radiation source 103 at the predetermined position. Alternatively the optical receiver 102b will cease receiving emitted optical signal from the lumen 101 in the presence of the radiation source 103 at the predetermined portion. Alternatively, the optical receiver 102b will receive an emitted optical signal of a different wavelength from the lumen 101 in the presence of the radiation source 103 at the predetermined portion. Alternatively the optical receiver 102b will receive an emitted optical signal of different intensity from the lumen 101 in the presence of the radiation source 103 at the predetermined portion.

The optical receiver 102b may be the tip of an optical fiber arranged for receiving an emitted signal from the lumen. Alternatively, such optical source 102a may comprise reflecting means, such one or more mirrors, or one or more selective mirrors, may be installed in a guiding means (e.g.: an optical fiber) such that a light signal is emitted in the lumen 101.

In use, following insertion of an object (e.g.: the radiation source 103) in the application device 100, once at the predetermined position, the radiation source 103 crosses the optical signal emitted in the lumen 101 by the optical source 102a. As a consequence of the radiation source 103 being at the predetermined position, the emitted optical signal to be received by the optical receiver 102b differs then when the radiation source 103 is not at the predetermined position such that an output signal indicative of whether or not the radiation source 103 is at a predetermined position in the lumen 101 is generated by the sensor element.

As mentioned above, the embodiment represented in FIG. 1b shows the optical source 102a and the optical receiver 103b positioned relative to each other to form an angle of 180 degrees in an axe perpendicular to the longitudinal axis of the applicator device. By the foregoing arrangement, a plurality of sensor elements 102, hence a plurality of combinations optical sources 102a and optical receivers 103b may be incorporated in an applicator device 100 such that several positions of interest are defined. Each and every of the combinations optical source 102a and optical receiver 102b are arranged to generated an output signal indicative of whether or not the radiation source 103 is at a predetermined position in the lumen 101.

In an alternative embodiment, the sensor element 102 may be an ultrasound sensor. In this embodiment, the sensor element 102 is configured to i) emit an ultrasound signal into the lumen 101, and ii) receive an emitted ultrasound signal from the lumen 101. The foregoing may be achieved by at least one ultrasound source 102a for emitting an ultrasound signal into the lumen 101 and one or more ultrasound receivers 102b for receiving emitted ultrasound signal from the lumen 101. Several means may be foreseen for the ultrasound source(s) 102a. The present invention is not limited to a specific, or a range of ultrasound wavelength; several ultrasound wavelengths that could be optimal for the aforementioned construction.

The ultrasound receiver 102b is arranged for receiving emitted ultrasound signal from the lumen 101 in the presence of the radiation source 103 at the predetermined position. Alternatively the ultrasound receiver 102b will cease receiving emitted ultrasound signal from the lumen 101 in the presence of the radiation source 103 at the predetermined portion. Alternatively, the ultrasound receiver 102b will receive an emitted ultrasound signal of a different wavelength from the lumen 101 in the presence of the radiation source 103 at the predetermined portion. Alternatively the ultrasound receiver 102b will receive an emitted ultrasound signal of different intensity from the lumen 101 in the presence of the radiation source 103 at the predetermined portion.

In an embodiment represented the ultrasound source 102a and the ultrasound receiver 103b positioned relative to each other to form an angle of 180 degrees in an axis perpendicular to the longitudinal axis of the applicator device. By the foregoing arrangement, a plurality of sensor elements 102, hence a plurality of combinations ultrasound sources 102a and ultrasound receivers 103b may be incorporated in an applicator device 100 such that several positions of interest are defined. Each and every of the combinations ultrasound source 102a and ultrasound receiver 102b are arranged to generated an output signal indicative of whether or not the radiation source 103 is at a predetermined position in the lumen 101.

A combination of all sensor elements 102 as defined above may be foreseen. For example, an applicator device 100 may comprise more than one sensor elements 102 may comprise at least one sensor element 102 comprising the combination of an optical source 102a and optical receiver 102*b* and at least one sensor element 102 comprising the combination of an ultrasound source 102*a* and ultrasound receiver 102*b*.

Figure 1C:
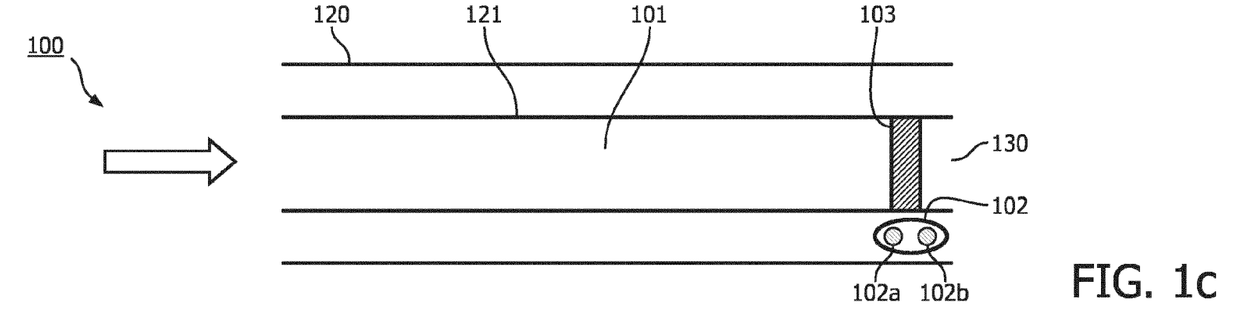

The embodiment schematically represented in FIG. 1*c* is an alternative embodiment whereby the optical source 102*a* and the optical receiver 102*b* are positioned for example on the same axis parallel to the longitudinal axis of the applicator device. Alternatively, the optical source 102*a* and the optical receiver 102*b* could consist of the same tip of an optical fiber, as it will be explained more in detail hereunder. For example, by the foregoing arrangement, the optical receiver 102*b* is arranged such that the optical signal received from the lumen is indicative whether or not said radiation source 103 is at the predetermined position. The latter may be achieved consequently of the reflective (or refractive) property of the radiation source 103. In this arrangement, the radiation source at the predetermined position will reflect the optical signal emitted into the lumen towards the optical receiver 103*b*. Alternatively, reflecting means are arranged to reflect the emitted optical signal by the signal source 102*a* such that the optical receiver 103*b* receives the reflected signal from the lumen 101 in the absence of the radiation source 103 being at the predetermined position. For example, this may be achieved by a reflective coating of the lumen side of the inner wall 121 of the applicator device 100. Alternatively the foregoing may be achieved by the one or more mirrors positioned to reflect the emitted optical signal from the lumen in the absence of the radiation source 103 being at the predetermined position. In those arrangements the emitted optical signal by the optical source 102*a* is reflected by the radiation source 103, or alternatively totally blocked by the radiation source 103 when at the predetermined position. This causes the emitted optical signal to be received from the lumen by optical receiver 103*b* to be of a different in intensity. Alternatively, the emitted optical signal to be received from the lumen by optical receiver 103*b* is of a different wavelength than the emitted optical signal by the signal source 102*a*. Alternatively, no emitted optical signal is received from the lumen by optical receiver 103*b* in view of the presence of the radiation source 103 at the predetermined position. In all the foregoing alternatives, the presence of the radiation source 103 at the predetermined position cause the signal element 102 to generate an output signal indicative of whether or not the radiation source 103 is at a predetermined position in the lumen 101. In this configuration, the emitted optical signal by the signal source 102*a* may be reflected, or refracted, or absorbed by the radiation source 103 when said radiation source 103 is at the predetermined position.

Alternatively, the foregoing may be achieved by one optical fiber (see FIG. 2) arranged to emitted an optical signal into the lumen (optical source 202*a*), and receive an emitted optical signal from the lumen (optical receiver 202*b*). In this arrangement, when said signal is reflected by either one or more mirrors such that the presence of the radiation source at the predetermined position blocks the emitted signal, such that no optical signal from the lumen is received by the optical fiber i.e.: the optical receiver).

Figure 2:
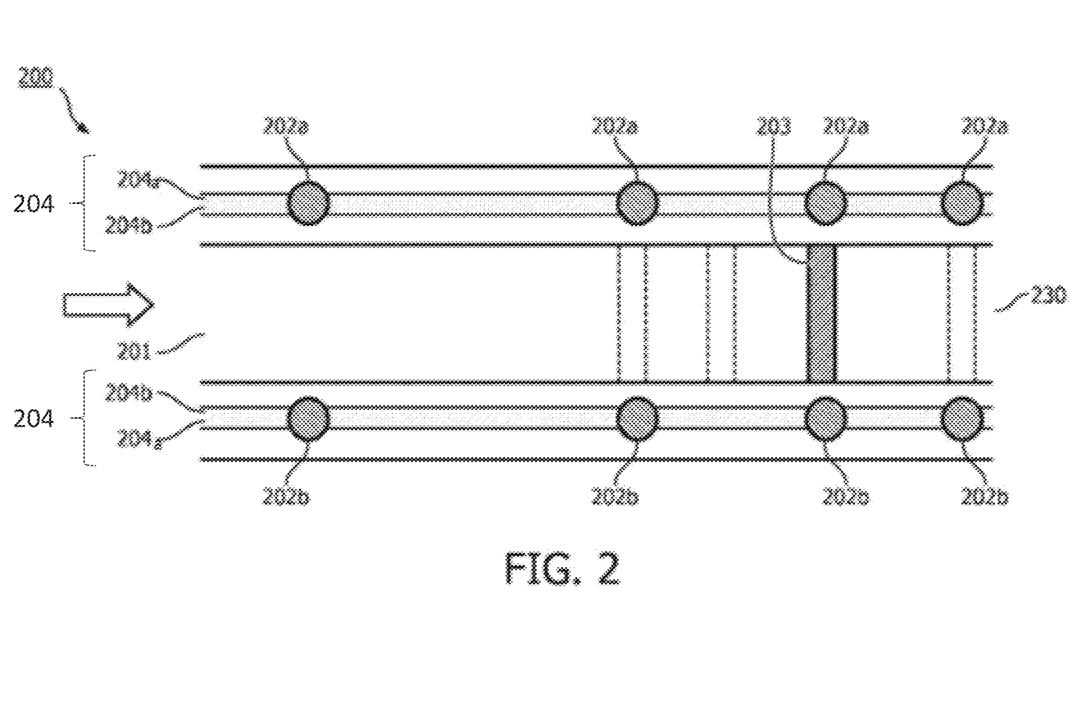
FIG. 2 schematically shows a cross-section view of an embodiment of the applicator device according to the present invention.

FIG. 2 schematically represents an alternative embodiment of the present invention. In this embodiment, an applicator device 200 comprises one or more optical fibers 204. An optical fiber 204 is a flexible, transparent fiber, generally made of silica or plastic, but other alternative are possible, such that it can serve as a waveguide (in other words a "light pipe") for transmitting an optical signal between the fiber's two ends. The applicator device 200 according to the present embodiment may comprise one, or alternatively two, or alternatively three, or alternatively four, or more optical fibers which are coupled (or optically coupled) to the one or more sensor elements 202. In further detailed, the optical fiber 204 may be coupled to one or more optical source 202*a* and/or one or more optical receivers 203*b*.

One or more optical fibers 204 may be arranged to follow the applicator device 200 longitudinally, preferably between the two ends (or tips, or opening) of said applicator device 200. This arrangement allows guidance of the optical signal (or light signal) along the length of the applicator device 200. For example with two optical fibers 204, a first optical fiber 204*a* is arranged for guiding an optical signal to be emitted into the lumen 201 of the applicator device 200. A second optical fiber 204*b* is arranged to receive an emitted optical signal from the lumen, and is further arranged to guide an output signal indicative of whether or not the radiation source 203 is at a predetermined position. It will be understood that by the foregoing arrangement, the output signal may be the emitted optical signal received from the lumen 201. In a preferred embodiment, the output signal is guided by the second optical fiber 204 towards a detector unit (not shown in FIG. 2).

In the foregoing arrangement with two optical fibers 204, the optical source 202*a* could be the tip (or the end) of the first optical fiber 204*a* (such that an optical signal guided by the optical fiber 204 is emitted in the lumen 101). Alternatively the optical source 202*a* could be a mirror arranged to reflect (part of) the optical signal guided by the first optical fiber 204*a* into the lumen 201. Alternatively the optical source 202*a* could be a selective reflector arranged to reflect a predetermined wavelength (or range of wavelengths) such that the optical signal is guided by the first optical fiber 204*a* into the lumen 201. The optical receiver 202*b* could be the tip of the second optical fiber 204*b* such that the emitted optical signal is received from the lumen 201 by the second optical fiber 204*b*. Said second optical fiber is further arranged to generate an output signal to be guided by the second optical fiber 204*b* toward a detector 411 (not shown in FIG. 2). This output signal being indicative of whether or not the radiation source 203 is at a predetermined position in the lumen 201. For example, in use, when the radiation source 203 blocks the emitted signal from the lumen such that the signal received by the optical receiver 204*b* is indicative of the radiation source 203 being at the predetermined position. In a preferred embodiment, the respective tips of the first and second optical fibers 204*a*, 204*b* are arranged such that the predetermined position is at the tip (or the end) 230 of the applicator device 200.

Alternatively, the first optical fiber 204*a* and the second optical fiber 204*b* may be optically coupled, such that only one optical fiber has an opening to receive and/or emit a signal outside the applicator device 200.

Alternatively, an arrangement with one optical fiber 204 may be foreseen. In this embodiment, said optical fiber comprises at least one reflector for reflecting (part of) the light signal guided by the optical fiber into the lumen 201. The one or more sensor elements 202 of this embodiment comprise a reflecting means (not shown) for reflecting the emitted optical signal from the lumen 101 back into the optical fiber 204, such that an output signal indicative of whether or not the radiation source 203 is at a predetermined position in the lumen 201 is generated. To enable the latter outcome, several arrangements of the optical source 204*a* are possible. Without limitation, the optical source 204 could be the tip of the optical fiber 204, or alternatively one or more selective reflectors inside the optical fiber 204, or alternatively one or more two-ways reflectors inside the optical fiber. The radiation source 103 at the predetermined position causes the light signal emitted into the lumen 201 to be blocked, or reflected, such that the optical receiver 202*b* is either not receiving an optical signal from the lumen 201. Alternatively, the optical receiver 202*b* receives a different intensity of optical signal from the lumen 201. Alternatively, the optical receiver 202*b* receives an optical signal of a different wavelength (or different wavelengths) from the originally emitted optical signal.

The one or more optical fibers 204 may comprise several combination of optical sources 202 *a* and optical receivers 202 *b* along the length one or more optical fibers 204. As described above, this arrangement could be characterized by a plurality of reflectors. In this arrangement, each combination of optical sources 202 a and optical receivers 202 *b* will generate an output signal indicative of whether or not the radiation source 203 is at a predetermined position in the lumen 201. The plurality of output signals may enable, when detected and processed, several to be outcome as it will be further described hereunder. In a preferred embodiment, each of the one or more optical sources 202*a* will be arranged to emit in the lumen 201 an optical signal consisting of a predetermined wavelength, or alternatively of a predetermined range of wavelength. This is possible when such one or more optical sources 202*a* comprise selective reflector (not shown) arranged for emitting one, or alternatively a small range of wavelength into the lumen 201. Each of those emitted wavelength, or wavelength range may be received by the associated optical receiver 202*b* which will generated an output signal dependent of the received emitted wavelength of the optical signal. This is easily conceivable as each and every optical receiver 202*b* will generated simultaneously an output signal indicative of whether or not the radiation source 203 is at a predetermined position in the lumen 201, whereby each and every output signal will be of a different wavelength (or range of wavelength) dependent of the wavelength emitted in the lumen 201 by the optical source 202*a* and received from the lumen 201 by the optical receiver 202*b*.

Figure 3A:
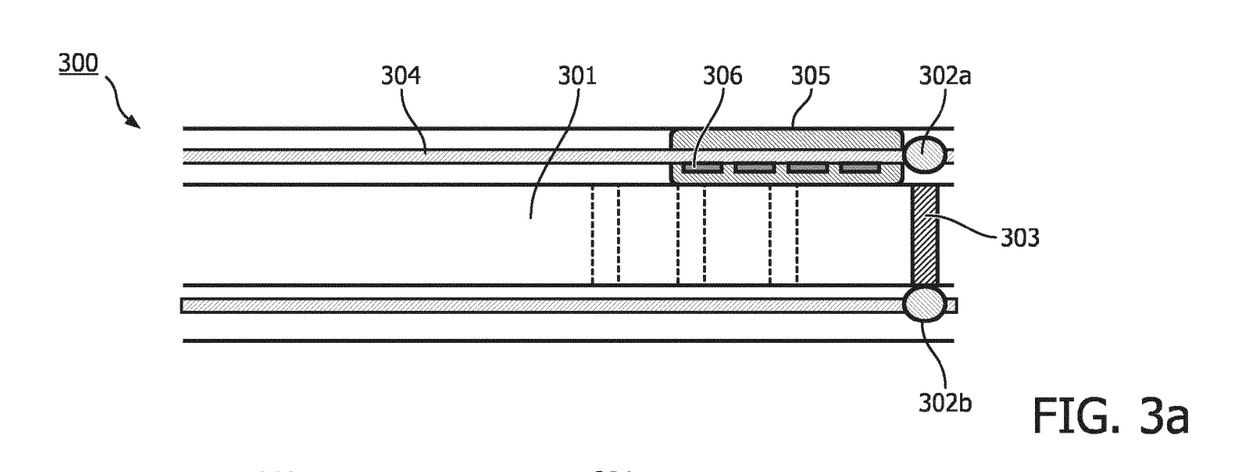

FIG. 3*a* schematically represents another embodiment of the applicator device 300 according to the present invention. The applicator device 300 comprises one or more optical fibers 304 comprising fiber Bragg grating 305, each fiber Bragg grating comprising a plurality of Bragg reflectors 306. Each Bragg reflector 306, which consists in a specific dielectric mirrors, reflects a specific wavelength, or alternatively a specific range of wavelengths. The use of a plurality of Bragg reflector generates a periodic variation in the refractive index of the optical fiber 304 as a whole. Bragg reflectors 306 can therefore be used as an inline optical filter to block certain wavelengths, or as a wavelength-specific reflector. Fiber Brag grating 305 may be used for as direct sensing elements for strain and temperature as it will be elucidated hereunder. Fiber Brag grating 305 may also be used as transduction element, converting the output of another sensor (e.g.: the output signal generated by the optical receiver 302*b*), as to determine a strain or temperature change of the applicator device 300.

Alternatively, the applicator device 300 is arranged such that the presence of the radiation source 303 at the tip of the applicator device 300 causes a strain. This strain is a result of the radiation source 303 being at the predetermined position. Consequently of this strain, a shift of the processed peak from the reflected wavelength for the fiber Bragg grating 305 will be induced. In this embodiment, the diameter of the lumen 301 is not constant throughout the length of the applicator device 300. In other words, a smaller diameter of the lumen 301 at a predetermined position is being proposed, causing a strain of the applicator device 300 when the radiation source 303 is at the predetermined position. In this arrangement, when the fiber Bragg grating 305 comprise one or more reflector at a preferred location, the strain will provoke a shift of the reflected wavelength(s) reflected by the fiber Bragg grating 305. This shift is indicative of the presence of the radiation source 303 at the predetermined position. The skilled in the art will see an advantage of this embodiment when the predetermined position is the tip of the applicator device 300. However, as fiber Bragg grating 305 is sensitive to a strain change, the aforementioned embodiment could alternatively or additionally be used for tracking of the radiation source 303 in the lumen 301. In the latter embodiment, the applicator device 300 comprises several locations where the diameter of the lumen 301 is narrower such that once the radiation source 303 positioned in such a narrower location, the resulting strain will make the fiber Bragg 305 generate an output signal indicative of the radiation source 303 being at the predetermined position.

In further details, the applicator device 300 may comprise a plurality of sensor elements 302 as to enable the generation of simultaneous output signal allowing tracking of the radiation source 303 in the lumen 300. The applicator device 300 may comprise 2, 5, 7, 8, 10 or more sensor elements 302, each generating an output signal indicative of whether or not the radiation source 301 is at a predetermined position. Alternatively, a subset of the plurality of sensor elements 302 may be used to determine a strain or a temperature change of the applicator device 300, while another subset of such plurality of sensor elements 302 may be used for tracking the radiation source 303. Alternatively, more than one optical sensor elements 302 could be arranged to generated output signals indicative of the movement of the radiation 303 source in the lumen 301 of the applicator device 300 and one or more ultrasound sensor elements 302 could be arranged to generate an output signal indicative of the radiation source 303 being at the tip of the applicator device 300. Other alternative combination of sensor elements 302 may be evident for the skilled person based on the present invention.

Figure 3B:
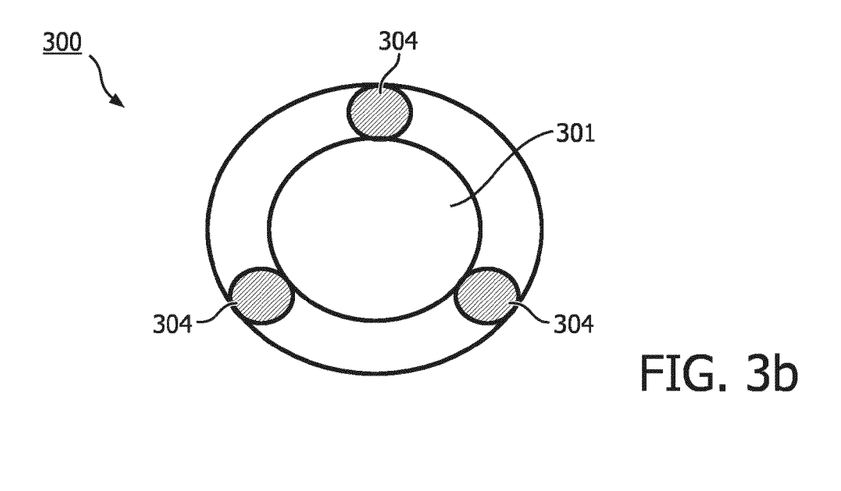

FIG. 3*b* schematically represents another embodiment of this invention. In this embodiment, the applicator device 300 comprises three optical fibers 304, each comprising at least one fiber Bragg grating 305 (each comprising a plurality of Bragg reflectors 306). The three optical fibers 304 are arranged parallel to the axis generated by applicator device 300 such that at least an angle of 120 degrees is formed between each of the three optical fibers 304 when measured from a line passing to the origin (the center) of the lumen. By this arrangement, when used with Bragg reflectors 306 which are specific to one wavelength, the arrangement of three optical fibers 304 as mentioned above enable computer reconstruction of the applicator device 303. In this arrangement, the peak of reflected wavelength for each of the Bragg reflectors 306 shifts as a consequence of the changes in strain of the applicator device 300. Such peaks may be detected when processed with a spectrum analyzer (not shown). In addition, such peaks may be further processed to compute, and therefore determine the shape of the applicator device 303 and the temperature along the applicator device 303.

In more details, this arrangement may comprise several selective Bragg reflectors 306, to generate one or more output signal indicative of the radiation source 303 being at the predetermined position in the lumen 301. Alternatively, this arrangement enables tracking of the movement of the radiation source 303 in the lumen 301 as described above. Alternatively, this arrangement allows for detecting a strain or temperature change of the applicator device 300. In order to detect a strain or temperature change of the applicator device 300, a preferred embodiment comprises several selective Bragg reflectors 306 (e.g. 8, 10, 12, 15) which are each selective for a particular wavelength (or a selected range of wavelength). As a matter of cost efficiency, it is submitted that it suffices to have 10 Bragg reflectors 306 on a distance of 20 cm of applicator device 300.

Figure 4:
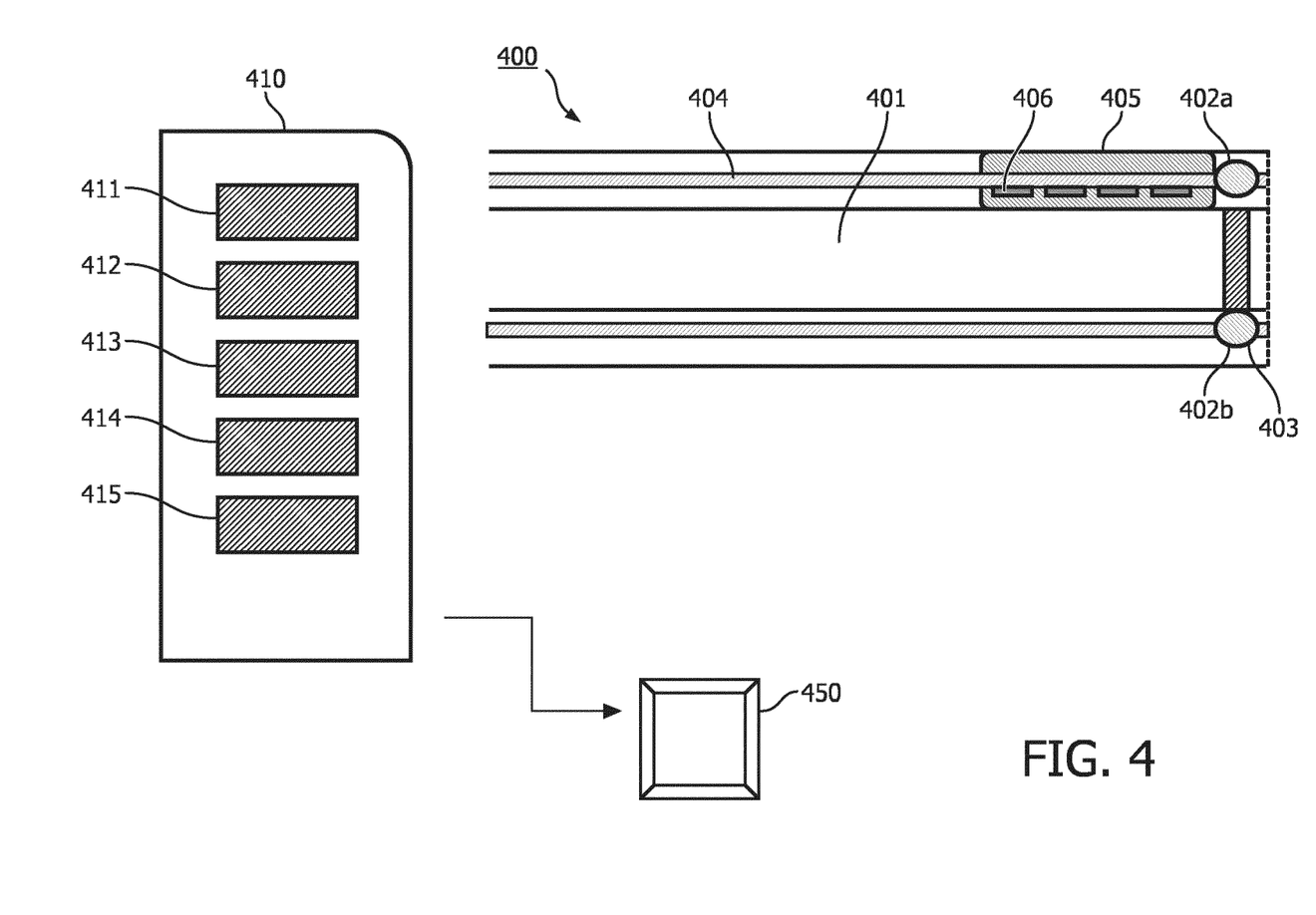
FIG. 4 schematically shows an embodiment of a system according to the present invention.

FIG. 4 schematically represents a system 410 for brachytherapy according to the present invention. The skilled in the art will understand that said system may comprise any of the embodiment of the applicator device 400 described herein and any equivalents thereof.

In an embodiment, the system 410 comprises a detector unit 411 configured to detect the output signal(s) generated by each of the one or more sensor elements 402 of the applicator device 400. The detector unit 411 is arranged to enable a user, or an operator to assess, from the signal thereby detected, if the radiation source 403 is at a predefined position in the lumen 401. Alternatively, said detector unit 411 may be arranged to transform a detected optical signal and/or alternatively a detected ultrasound signal into an electric signal, or any other signals capable of being processed by a processor unit 414, or alternatively any other units. The skilled person would be able to foresee several types of detector unit 411 which can achieve the foregoing.

In an embodiment, the detector unit 411 is configured to detect and identify each wavelength of the output signal. In this embodiment, the detected signal generated is indicative of the wavelength of the output signal.

In an embodiment, when the applicator device 400 comprises fiber Bragg grating 405, as further detailed above, the detector unit 411 is arranged to detect the amplitude of the peak of the reflected wavelength.

Alternatively or additionally, the system 410 further comprises a tracking unit 412. Said tracking unit is configured to track (to follow the movement, the displacement) the radiation source 403 into the lumen 401. In an embodiment where the applicator device 400 comprises a plurality of sensor elements 402, the tracking 412 unit is configured for receiving the detected output signals from the detector. A succession in time of detected output signal will be translated by the tracking unit 412 into a tracking of the radiation source 403 in the lumen. In further details, by this arrangement, the skilled person will foresee that the different output signals from a plurality of sensor elements 402 may be of different wavelengths (or wavelengths range). Those different wavelengths or wavelengths range are capable of being detected by the detecting unit 411 and translated into the tracking of the applicator device 400 by the tracking unit 412. Alternatively, the output signal may be generated at different time which will be detected by the detecting unit 411 and translated into tracking of the radiation source 403. In further details, the movement of the radiation source 403 in the applicator device 400 generates a plurality of output signals by the plurality of sensor elements 402, each output signals which are indicative of different positions of the radiation source 403 into the lumen (indicative of the radiation source 403 being at a predefined position).

Alternatively or additionally, the tracking unit 411 may allow tracking of the radiation source 403 from the output signal generated following continuous selective reflection of the Bragg reflectors 405 as detected by the detector unit 411.

Alternatively or additionally, the tracking unit and the detecting unit may be one single unit.

In another embodiment, the system 410 comprises a signal generator 413 coupled to the applicator device. The signal generator is arranged to generate a generated signal which will be totally, or alternatively partially emitted into the lumen. In a preferred embodiment, the signal generator 413 is coupled, or alternatively optically coupled, to one or more optical fibers 404. Said one or more optical fibers 404 are arranged to guide said generated optical signal to the optical source 402a of the signal element 402. The signal source 402a is arranged to emit, from the generated optical signal, an emitted optical signal into the lumen. In an embodiment comprising a plurality of signal source 402a, said generated signal may be partially reflected into the lumen 401 by a signal source 402a, while the non-reflected part will continue into the optical fiber 404 until the next signal source 402a. It will be clear to the skilled in the art that when each of the signal source 404a is a selective reflector, only part of the generated signal will be reflected and the remaining of said generated signal will continue in the optical fiber 404.

In further details, said signal generator 413 may be arranged to generated a light signal which may be of one or more predefined (or preselected) wavelengths or wavelength range(s), wherein said one or more optical signals are generated simultaneously or successively. The range of wavelengths emitted by the signal generator 413 is an important parameter defining the accuracy and resolution for the shape sensing, the temperature sensing and tracking of the radiation source 403. Alternatively, the signal generator 413 is configured to generate dynamic variation in the wavelengths of light emitted into the lumen via the optical source 402a via the one or more optical fibers 404.

In another embodiment, the system 410 comprises a processing unit 414 arranged to process the detected output signals as to determine a) a temperature and/or shape of the applicator device 400, or b) a change in the temperature and/or the shape of the applicator device 400 resulting from the radiation source 403 being (i) deployed into the lumen 401, and/or (ii) at the predetermined position, and/or (iii) retrieved out of the lumen. This process may be advantageously done using the fiber Bragg grating 405 output signals. Alternatively to the fiber Bragg grating 405, the foregoing process but may be achieved via Rayleigh scattering.

In an embodiment, the processing unit 414 comprises a spectrum analyzer or any alternative measurement means to measure the magnitude of the light signal versus frequency within the full frequency range of the applicator device 400. A spectrum analyzer of 20 Hz allows analysis of the detected output signal indicative of a temperature change, and/or a shape change of the applicator device 400. A spectrum analyzer of about 300 Hz allows analysis of the tracking of the radiation source 403 in the lumen 401.

In more details, the spectrum analyzer is configured to receive the detected signal from the detector unit 411 such that that the presence or the absence of the radiation source 403 at the predetermined positions will be determined. Alternatively, the spectrum analyzer is configured to receive a plurality of signal per second, whereby a peak change of wavelength can be inferred. The skilled person will foresee several means that will be capable of acting as a spectrum analyzer, but it is to be seen understand that the resolution of spectrum analyzers will also be a key parameter defining the accuracy and resolution for shape, temperature and HDR source tracking.

For example, the processing unit 414 may be arranged to process the received and detected amplitude (at specific wavelengths) of one or more detected signals. Alternatively, the processing unit 414 may be arranged to simultaneously process shifts in the wavelengths of the reflected peaks in the detected output signals to determine if the radiation source 403 is at a predetermined position, but may also be, in cooperation with the tracking unit 411 used to track the movement of the radiation source in the lumen 401. More advanced, dynamic processing methods may be relevant, especially in combination with varying light sources.

If the embodiment of the applicator device 400 comprises fiber Bragg grating 405, and Bragg reflectors 406, the processing unit 414 may be arranged to processed the different detected signals from the detector 411 such that a detected signals, or part of a detected signals are used to determined shape and temperature sensing, while another part of the detected signal or, another detected signal, which could be the one generated from a fiber Bragg grating 405 or alternatively Bragg reflector 406 positioned at the tip 430 of the applicator device in the vicinity of the tissue to irradiate such that this output signal is used to determine whether the radiation source 403 is present at a predetermined position.

For example, once detected by the detector 411, the processing unit 414 may be arranged to process the reflected signal from different Bragg reflectors 406 (the output signals), said different detected output signals being processed to be indicative of a temperature change as explained above and/or a shape change as described above and/or that the radiation source 403 is present or not at a predetermined position.

The strain (strain is a normalized measure of deformation representing the displacement between particles in the body relative to a reference length) and the temperature may be determined by the processor as described hereunder. The output signal detected by the detector unit 411 is understood by the processor as a measurement that causes a shift in the Bragg wavelength, $\Delta\lambda_B$. The relative shift in the Bragg wavelength, $\Delta\lambda_B/\lambda_B$, due to an applied strain (e) and a change in temperature ($\Delta T$) is approximately given by the following, where $C_S$ is the coefficient of strain, which is related to the strain optic coefficient $P^e$. Also, $C_T$ is the coefficient of temperature, which is made up of the thermal expansion coefficient of the optical fiber, $\alpha_\Lambda$, and the thermo-optic coefficient, $\alpha_n$, $$\left[\frac{\Delta\lambda_B}{\lambda_B}\right] = C_S\epsilon + C_T\Delta T$$

or, $$\left[\frac{\Delta\lambda_B}{\lambda_B}\right] = (1 - P_e)\epsilon + (\alpha_\Lambda + \alpha_n)\Delta T$$

In another embodiment, the system 410 further comprises an alarm generator 415 arranged to generate an alarm signal when the detected output signal is indicative of the radiation source 403 being at a predetermined position, or alternatively not being at the predetermined position. For example, this alarm signal may be generated when the time between the loading of the radiation source 403 into the applicator device 400 and said radiation source 403 reaching a predetermined position is not what it is supposed to be (which is standard for a known length of the applicator device and a protocol of the system 410). In the foregoing example, the alarm generator 415 will be triggered when the detector unit 411 will receive an output signal, or not receive an output signal, indicative of the radiation source 403 not being at the predetermined position.

It will be understood that to the extent the applicator device 400 is configured to comprise several predetermined positions, the alarm generator 415 may be triggered by only one of those predetermined positions, all of those predetermined positions, or any known number of predetermined positions. In addition, the number of predetermined position which could trigger an alarm could be configured differently for every protocol run, for example when the system 410 is used for brachytherapy treatment on different patients, or for different fractions of treatment on a same patient. Said alarm signal could be an audio signal, a light signal, a combination of both, or any other signal that would trigger a user, or an operator to react. It will be understood that the alarm will enable the user to act upon known meaning of the alarm, where, for example, if the alarm generator 415 is arranged to generate an alarm when the radiation source 403 has not reach a predetermined position, the radiation source 403 will be retrieve from the lumen 401 of the applicator device 400.

In another embodiment, the system 410 comprises a display, or a user interface 450 which enables the user, or the operator to get information on a visual form. As non-limiting examples, such user interface 450 could be a built-in screen, or a stand-alone screen connected via wires, or wirelessly with other component of the system 410 such that said user interface 450 is arranged to receive the information to be visually represented for ease of use of the system 410 by the use. For example, the user interface 450 could enable the user to visually see the output of the alarm generator 415. Alternatively, or simultaneously, the user interface 450 could enable a visual representation of the output of the tracking unit 411, or the processing unit 412, whereby the strain and/or temperature change detected and measured could be made available on an alphanumeric or graphical representation.

Alternatively, such user interface 450 may be used for entering commands into the system 410. Such comments can be for example a protocol, a treatment plan, or any specific instruction that would enable the system 410 to act per the expectation of the user, or the operator.

In a yet further embodiment, the system 410 further comprises a delivery device (not shown) configured to perform at least one of the action selected from the group consisting of (i) deploying at least one radiation source 403 into the lumen 401 of the applicator device 400 for irradiating the region of interest and (ii) retrieving the at least one radiation source out of the region of interest via the lumen 401 of the applicator device 400, wherein the delivery device (not shown) includes one or more radiation source feed devices, wherein the one or more radiation source feed devices include a cable having a radiation source 403 coupled to a tip portion of the cable.

Figure 5:
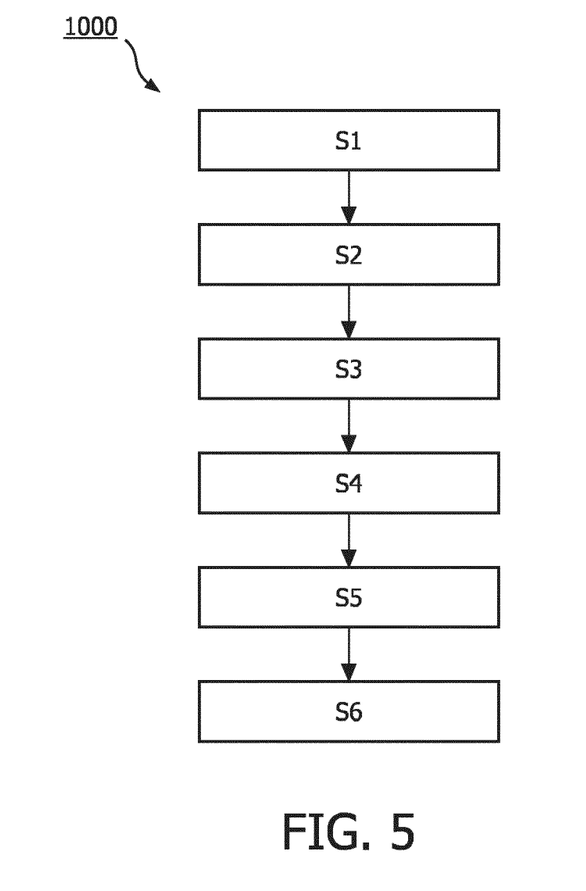
FIG. 5 schematically shows an embodiment of a method according to the present invention.

FIG. 5 represents flow chart representing a method 1000 for assessing if whether or not a radiation source is at a predetermined position in a lumen of an applicator device according to the present invention. Said method to be carried on by a system may enable complete automation of such system, where the user would receive all relevant information on a user interface 450.

The schematically shown in FIG. 5 comprises a first step S1 which is to provide an applicator device according to the present invention. In a preferred embodiment, the applicator device will be provided such that its tip reaches a region of interest. For example, such region of interest may be a tumorous tissue to be irradiated, or any other object that should be irradiated.

Said method comprises a second step S2, said steps being characterized in providing a radiation source in the lumen of the applicator device according to the present invention. For example, by S2, a radiation source inside the afterloader is guided into the lumen of the applicator device. For example, the radiation source could be guided into the lumen of the applicator device via a mechanic means enabling said radiation source to reach the tip of said applicator device (for example via a wire). Alternatively, S2 could be such that the source is provided and retrieved by a pressure difference inside the lumen.

Said method comprises a third step S3, said step being characterized in assessing, on the basis of the output signal, whether or not the radiation source is at the predetermined position. This step may be achieved, without limitation, by any means detailed in the present document from the detection of an output signal received from the applicator device.

Additionally, said method may comprise a fourth step S4, said step being characterized in tracking the movement, or the displacement of the radiation source inside the lumen of the applicator device. As elucidated earlier, said tracking of the radiation source can, for example, be achieved by the detection and/or the processing of simultaneous output signals, wherein said output signals are indicative of the radiation source being a predetermined position in the lumen of the applicator device.

Additionally or alternatively, said method may comprise a fifth step S5, said step being characterized in signaling, or alarming when the radiation source is, or is not at a predetermined position. For example, by S5 may provide for an alarm signal to alert the user of the radiation source reaching, in a given time, the tip of the applicator device.

Additionally or alternatively, said method may comprise a sixth step S6, said step is the processing of the output signal such that a shape change, or additionally or alternatively a temperature change is determined. As detailed above, several means can be foreseen by the skilled person to detect a shape change or temperature change, wherein S6 is not limited by the means disclosed herein.

It is clear from the aforementioned description that steps S4, S5 and S6 may be in a different order, such that, for example, step S6 precedes step S4. Alternatively, the order could be that step S5 is the last step carried by the method, where steps S6 and S4 precede step S5, in any order. Alternatively, step S4 is the last step carried by the method, where steps S5 and S6 precede step S4, in any order.

The method depicted in FIG. 5, or alternately described above, may be carried by computer program comprising program code means, when executed, for causing a system for interventional brachytherapy to work according to the method described above.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A device for interventional brachytherapy, comprising:
    an applicator device configured to be inserted into, or near a region of interest within a living body, the applicator device comprising an inner wall and an outer wall, the applicator device defining a lumen for receiving a radiation source; and
    an optical sensor configured to generate an output signal indicative of whether or not the radiation source is at a predetermined position within the lumen, the optical sensor including an optical source for emitting an optical signal into the lumen and an optical receiver configured to receive the emitted optical signal from the lumen;
    wherein the optical sensor is at least one of:
    located between the inner wall and the outer wall of the applicator device; or
    coupled to the inner wall while being located at least partially inside the lumen;
    or
    located fully inside the lumen;
    wherein the optical source and the optical receiver are positioned relative to each other to either, while the radiation source is at the predetermined position by one of:
        block the emitted optical signal from reaching the optical receiver; or
        redirect the emitted optical signal to the optical receiver;
        wherein the optical signal received by the optical receiver when the radiation source is at the predetermined position within the lumen differs from when the radiation source is not at the predetermined position within the lumen.

2. The device as claimed in claim 1, further comprising:
    first and second optical fibers for causing a light signal to be guided through the length of the applicator device, said first optical fiber being coupled to the optical source and said second optical fiber being coupled to the optical receiver.

3. The device as claimed in claim 2, wherein a plurality of fiber Bragg gratings are dispersed along a length of each of the first and second optical fibers, the optical signal being reflected by the plurality of fiber Bragg gratings to derive a temperature and/or strain of the applicator device.

4. The device as claimed in claim 1, further including a second optical sensor, wherein the optical sensor and the second optical sensor are arranged to generate the output signal to enable tracking of a movement of the radiation source in the lumen.

5. The system as claimed in claim 1, further comprising:
    a processing unit arranged to process the output signal to determine:
    a) a temperature and/or shape of the applicator device, or
    b) a change in the temperature and/or the shape of the applicator device resulting from the radiation source being (i) deployed into the lumen, and/or (ii) at the predetermined position, and (iii) retrieved out of the lumen.

6. A system for interventional brachytherapy, comprising:
an applicator device configured to be inserted into, or near a region of interest within a living body, the applicator device comprising an inner wall and an outer wall, wherein the applicator device defines a lumen for receiving a radiation source and a plurality of optical sensors, each optical sensor being configured to generate an output signal into the lumen, the output signal being indicative of whether or not the radiation source is at a predetermined position within the lumen;
each optical sensor including an optical source for emitting an optical signal into the lumen and an optical receiver configured to receive the emitted optical signal from the lumen;
wherein the optical sensor is at least one of:
  located between the inner wall and the outer wall of the applicator device; or coupled to the inner wall while being located at least partially inside the lumen; or
  located fully inside the lumen;
a plurality of optical receivers configured to receive the emitted output signal from the lumen, wherein the plurality of optical sensors and the plurality of optical receivers are positioned relative to each other while the radiation source is at the predetermined position to either: (i) block the emitted output signal blocked from reaching the plurality of optical receivers; or (ii) redirect the emitted output signal to the plurality of optical receivers; and
a detector configured to detect the output signal generated by each of the plurality of optical sensors.

7. The system as claimed in claim 6, further comprising:
a tracking unit configured to track movement of the radiation source in the lumen, said tracking unit being arranged to track the radiation source in the lumen based on the detection of the output signal.

8. The system as claimed in claim 7, further comprising:
a signal generator arranged to generate a generation signal to be communicated to the lumen, wherein the signal generator is arranged to generate one or more optical generation signals of a predefined wavelength or wavelength range and wherein the signal generator is arranged to generate said one or more optical generation signals simultaneously or successively.

9. The system as claimed in claim 6, further comprising a user interface unit for representing the position of the radiation source in the lumen.

10. The system as claimed in claim 6, further comprising:
an alarm generator unit configured to generate an alarm while the position and/or the movement of the radiation source in the lumen violates a predetermined limit based on the output signal.

11. A method for assessing a position of a radiation source at a predetermined position within a lumen of an applicator device, said method comprising:
wherein the applicator device comprises an inner wall and an outer wall, the applicator device defining the lumen for receiving the radiation source;
positioning the radiation source into the lumen of the applicator device inserted adjacent a region of interest in a living body,
generating, with one or more optical sensors of the applicator device, an output signal indicative of whether or not the radiation source is at the predetermined position within the lumen, each optical sensor including an optical source for emitting an optical signal into the lumen and an optical receiver configured to receive the emitted optical signal from the lumen; and
wherein the optical sensor is at least one of:
  located between the inner wall and the outer wall of the applicator device; or
  coupled to the inner wall while being located at least partially inside the lumen, or
  located fully inside the lumen;
assessing on the basis of the output signal, whether or not the radiation source is at the predetermined position, wherein each optical sensor generates the output signal by one of:
  blocking the emitted optical signal from reaching the optical receiver; or
  redirecting the emitted optical signal to the optical receiver;
  wherein the optical signal received by the optical receiver when the radiation source is at the predetermined position differs from when the radiation source is not at the predetermined position.

12. A non-transitory computer readable medium comprising instructions executable by a computer to carry out the steps of the method as defined in claim 11.

* * * * *